(12) United States Patent
Osawa et al.

(10) Patent No.: US 9,012,582 B2
(45) Date of Patent: Apr. 21, 2015

(54) TRANSPARENT HIGH-REFRACTIVE-INDEX RESIN COMPOSITION

(75) Inventors: Kenichi Osawa, Funabashi (JP); Takuro Oda, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 607 days.

(21) Appl. No.: 13/390,052

(22) PCT Filed: Aug. 6, 2010

(86) PCT No.: PCT/JP2010/063354
§ 371 (c)(1),
(2), (4) Date: Feb. 10, 2012

(87) PCT Pub. No.: WO2011/018990
PCT Pub. Date: Feb. 17, 2011

(65) Prior Publication Data
US 2012/0142878 A1   Jun. 7, 2012

(30) Foreign Application Priority Data
Aug. 13, 2009   (JP) .................. 2009-187697

(51) Int. Cl.
C08F 226/06   (2006.01)
C07D 251/70   (2006.01)
C07D 251/46   (2006.01)
C07D 251/30   (2006.01)
C09D 133/14   (2006.01)
C07D 251/34   (2006.01)
C07D 251/52   (2006.01)
(Continued)

(52) U.S. Cl.
CPC ............ C09D 133/14 (2013.01); C07D 251/34 (2013.01); *C08F 220/36* (2013.01); C07D 251/46 (2013.01); C07D 251/52 (2013.01); C07D 251/54 (2013.01)

(58) Field of Classification Search
CPC .. C07D 251/46; C07D 251/48; C07D 251/52; C07D 401/04; C07D 401/12; C07D 251/54; C07D 413/12; C07D 257/02
USPC ........................ 526/261; 544/197, 211, 219
See application file for complete search history.

(56) References Cited

U.S. PATENT DOCUMENTS 7,985,476 B2   7/2011   Kurino et al.
2007/0059612 A1   3/2007   Yoshioka et al.

FOREIGN PATENT DOCUMENTS

JP   5-164901 A   6/1993
JP   7-157474 A   6/1995
(Continued)

OTHER PUBLICATIONS

International Search Report, PCT/JP2010/063354, Sep. 7, 2010.

*Primary Examiner* — Ling Choi
*Assistant Examiner* — Chun-Cheng Wang
(74) *Attorney, Agent, or Firm* — Birch, Stewart, Kolasch & Birch, LLP

(57) ABSTRACT

A resin with a favorable index of refraction and transparency even without using heavy atoms or inorganic oxide fine particles by means of a polymerizable monomer having a 1,3,5-triazine ring represented by formula 1.

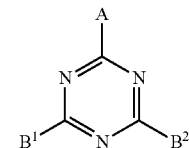

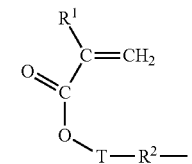

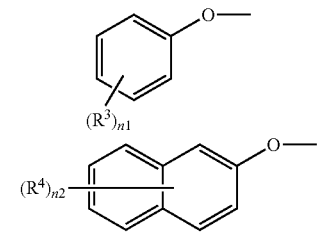

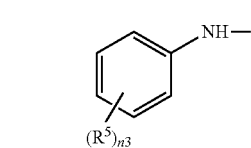

(In formula 1: A is a group represented by formula 2, (in formula 2: $R^1$ represents a hydrogen atom or a methyl group, T represents an alkylene having 1-10 carbon atoms, and $R^2$ represents O or NH), and B1 and B2 are each independently groups represented by formula 3, formula 4, or formula 5 (in formulas 3-5: $R^3$, $R^4$, and $R^5$ represent an alkyl group having 1-10 carbon atoms, an aryl group, or an aryloxy group, n1 and n3 are integers from 0-5, and n2 is an integer from 0-7, however when there are at least two of each of $R^3$, $R^4$, and $R^5$, these may be the same or different from each other).)

3 Claims, No Drawings

(51) Int. Cl.
  *C07D 251/54* (2006.01)
  *C08F 220/36* (2006.01)

(56) References Cited

FOREIGN PATENT DOCUMENTS

| | | |
|---|---|---|
| JP | 7-206832 A | 8/1995 |
| JP | 8-193180 A | 7/1996 |
| JP | 2002-155116 A | 5/2002 |
| JP | 2005-350531 A | 12/2005 |
| JP | 2007-270099 A | 10/2007 |
| JP | 2007-308631 A | 11/2007 |
| JP | 2009-013169 A | 1/2009 |
| JP | 2009013169 A * | 1/2009 |
| WO | WO 2005/037926 A1 | 4/2005 |

* cited by examiner

TRANSPARENT HIGH-REFRACTIVE-INDEX RESIN COMPOSITION

TECHNICAL FIELD

The present invention relates to a polymerizable monomer having a 1,3,5-triazine ring and also to a highly transparent high-refractive-index resin composition made thereof.

BACKGROUND ART

Being superior to glass in lightness and processability, such transparent resins as (meth)acrylic resin (e.g., polymethyl methacrylate), clear epoxy resin, and clear silicone resin have been widely used for aircraft windshields, clear containers, and clear coating materials.

Recently, they also have found use as transparent resin lenses for spectacle glasses in the optical field.

Also, in the field of optoelectronic materials, the aforesaid transparent resins are being commonly used for antireflective coating of liquid crystal displays, transparent coating of solar cells, light-emitting diodes, and CCD and CMOS sensors. Such optoelectronic materials usually need not only transparency but also high refractive indices for efficient light emission and light collection.

Unfortunately, conventional transparent resins are given somewhat controlled mechanical properties by crosslinking or the like but they need special techniques if they are to have improved optical properties, especially refractive index.

Such special techniques include addition of a large amount of such heavy atoms as bromine and sulfur to an organic resin for its improvement in refractive index, as disclosed in Patent Documents 1 and 2.

Another way for improvement of refractive index is by dispersion of high refractive inorganic oxide fine particles into an organic resin, as disclosed in Patent Documents 3 and 4.

The technique disclosed in the foregoing Patent Documents 1 and 2 suffers the disadvantage that the resulting organic resin is unstable to heat and light and vulnerable to degradation, such as discoloration, after use for a long period of time. In addition, the resulting organic resin is liable to corrode electrodes when it is used for electronic parts.

Also, the technique disclosed in Patent Documents 3 and 4 involves problems with long-term storage stability in the resulting resin containing fine particles dispersed therein. Moreover, it needs a large amount of dispersing stabilizer that ensures the stable dispersion of inorganic oxide fine particles in the resin. This poses a problem with balancing the refractive index against the dispersion stability.

Incidentally, there is known a resin composition (not intended for high refractive index) produced from a polymerizable triazine compound, as disclosed in Patent Documents 5 and 6.

PRIOR-ART DOCUMENTS

Patent Documents

Patent Document 1: JP-A H05-164901
Patent Document 2: JP-A 2005-350531
Patent Document 3: JP-A 2007-270099
Patent Document 4: JP-A 2007-308631
Patent Document 5: JP-A H07-157474
Patent Document 6: JP-A H07-206832

SUMMARY OF THE INVENTION

Problems to be Solved by the Invention

The present invention was completed in view of the foregoing. It is an object of the present invention to provide a polymerizable monomer that can give rise to a resin having a high refractive index without incorporation with inorganic oxide fine particles or heavy atoms and also to provide a transparent high-refractive-index resin composition produced from said monomer.

Means for Solving the Problems

As the result of extensive studies to achieve the foregoing objectives, the present inventors found that a polymerizable monomer having a specific 1,3,5-triazine ring can give rise to a transparent high-refractive-index resin, and this finding led to the present invention.

The gist of the present invention resides in the following.

1. A polymerizable monomer having a 1,3,5-triazine ring represented by Formula (1) below.

[Chemical Formula 1]

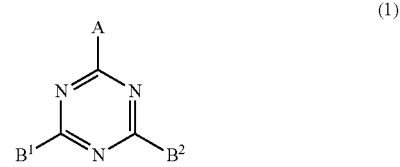
(1)

(where A denotes a group represented by Formula (2) below,

[Chemical Formula 2]

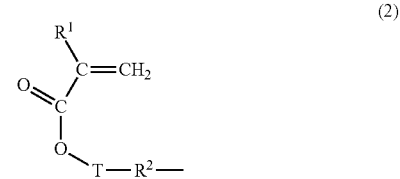
(2)

in which $R^1$ denotes a hydrogen atom or methyl group, T denotes a $C_{1-10}$ alkylene group, and $R^2$ denotes O or NH; and $B^1$ and $B^2$ mutually independently denote those groups represented by Formula (3), Formula (4), or Formula (5) below,

[Chemical Formula 3]

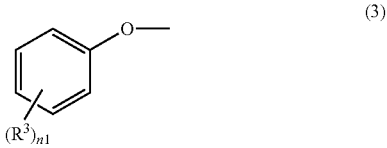
(3)

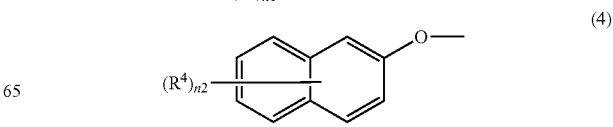
(4)

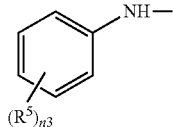

in which $R^3$, $R^4$, and $R^5$ each denote a $C_{1-10}$ alkyl group, aryl group, or aryloxy group, n1 and n3 are integers of 0 to 5, and n2 is an integer of 0 to 7, provided that $R^3$, $R^4$, and $R^5$ each in plural numbers may be identical with or different from one another.)

2. A high-refractive-index resin composition which is obtained by copolymerization of 70 to 100 parts by weight of the polymerizable monomer defined in Paragraph 1 above and 0 to 30 parts by weight of additional polymerizable monomer.

3. The high-refractive-index resin composition defined in Paragraph 2 above in which the additional polymerizable monomer is at least one species selected from vinyl monomer, acrylic monomer, methacrylic monomer, allyl monomer, and maleic acid monomer.

4. The high-refractive-index resin composition defined in Paragraph 2 or 3 above which contains 0.1 to 20 parts by weight of at least one species of crosslinking agent selected from epoxy compounds, isocyanate compounds, and aminoplast compounds, for 100 parts by weight of the resin in the resin composition.

Advantageous Effects of the Invention

The present invention provides a polymerizable monomer which gives rise to a resin composition which is composed of carbon, hydrogen, nitrogen, and oxygen as fundamental elements and which excels in transparency and has a refractive index higher than 1.57 at the wavelength of 633 nm. The resin composition yields a highly heat-resistant resin film owing to the 1,3,5-triazine skeleton positively introduced thereinto.

Thus, the resin composition can be used as a coating material which yields a resin film having a high refractive index and excelling in clarity, solvent resistance, and heat resistance.

EMBODIMENT FOR CARRYING OUT THE INVENTION

The following is a detailed description of the present invention.

The polymerizable monomer having a 1,3,5-triazine ring of the present invention is represented by Formula (1) below.

[Chemical Formula 4]

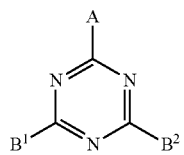

Where A denotes the group represented by Formula (2) below.

[Chemical Formula 5]

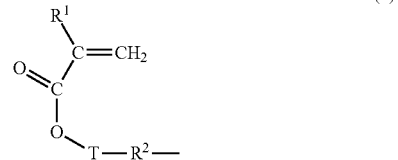

The above $R^2$ denotes a hydrogen atom or methyl group, T denotes a $C_{1-10}$ alkylene group, and $R^2$ denotes O or NH.

Here, $C_{1-10}$ alkylene group may be any of linear, branched, or cyclic ones, as exemplified by divalent groups corresponding to $C_{1-10}$ alkyl groups (detailed later). Preferable among them are ethylene group, propylene group, isopropylene group, and butylene group.

$B^1$ and $B^2$ mutually independently denote those groups represented by Formula (3), Formula (4), or Formula (5) below.

[Chemical Formula 6]

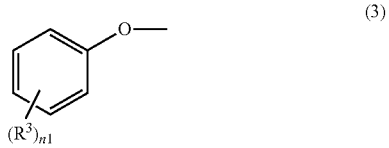

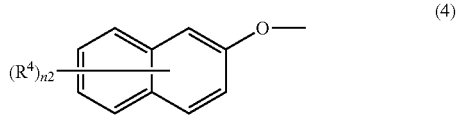

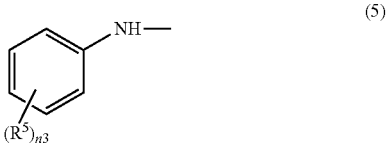

The above $R^3$, $R^4$, and $R^5$ each denote a $C_{1-10}$ alkyl group, aryl group, or aryloxy group, n1 and n3 are integers of 0 to 5, and n2 is an integer of 0 to 7, provided that $R^3$, $R^4$, and $R^5$ each in plural numbers may be identical with or different from one another. That is, two or more groups collectively represented by $R^3$, $R^4$, or $R^5$ may be the same or a combination of different substituents.

The above-mentioned $C_{1-10}$ alkyl group may be any of linear, branched, or cyclic ones. It includes, for example, methyl, ethyl, n-propyl, i-propyl, cyclopropyl, n-butyl, i-butyl, s-butyl, t-butyl, cyclobutyl, 1-methyl-cyclopropyl, 2-methyl-cyclopropyl, n-pentyl, 1-methyl-n-butyl, 2-methyl-n-butyl, 3-methyl-n-bntyl, 1,1-dimethyl-n-propyl, 1,2-dimethyl-n-propyl, 2,2-dimethyl-n-propyl, 1-ethyl-n-propyl, cyclopentyl, 1-methyl-cyclobutyl, 2-methyl-cyclobutyl, 3-methyl-cyclobutyl, 1,2-dimethyl-cyclopropyl, 2,3-dimethyl-cyclopropyl, 1-ethyl-cyclopropyl, 2-ethyl-cyclopropyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, cyclohexyl, 1-methyl-cyclopentyl, 2-methyl-cyclopentyl, 3-methyl-cyclopentyl, 1-ethyl-cyclobutyl, 2-ethylcyclobutyl, 3-ethyl-cyclobutyl, 1,2-dimethyl-cyclobutyl, 1,3-dimethyl-cyclobutyl, 2,2-dimethyl-cyclobutyl, 2,3-dimethyl-cyclobutyl, 2,4-dimethyl-cyclobutyl, 3,3-dimethyl-cyclobutyl, 1-n-propyl-cyclopropyl, 2-n-propyl-cyclopropyl, 1-i-propyl-cyclopropyl, 2-i-propyl-cyclopropyl, 1,2,2-trimethyl-cyclopropyl, 1,2,3-trimethyl-cyclopropyl, 2,2,3-trimethyl-cyclopropyl, 1-ethyl-2-methyl-cyclopropyl, 2-ethyl-1-methyl-cyclopropyl, 2-ethyl-2-methyl-cyclopropyl, and 2-ethyl-3-methyl-cyclopropyl groups.

Although the aryl group mentioned above is not specifically restricted in carbon number, it should preferably have a carbon number of 6 to 20. It typically includes phenyl group, naphthyl group, and anthranyl group. Preferable among them is phenyl group.

Although the aryloxy group mentioned above is not specifically restricted in carbon number, it should preferably have a carbon number of 6 to 20. It typically includes phenoxy group, naphthoxy group, and anthranyloxy group. Preferable among them is phenoxy group.

Incidentally, the aryl group and aryloxy group mentioned above may be used as an alkylated aryl group and alkylated aryloxy group respectively, which are substituted with the above-mentioned alkyl group.

The polymerizable monomer represented by Formula (1) above may have its groups $B^1$ and $B^2$ replaced by alkoxyl groups instead of the substituents represented by Formulas (3) to (5). However, the resulting monomer gives rise to a resin which has excels in transparency but has a low refractive index.

On the other hand, polymerizable monomers having $B^1$ and $B^2$ replaced with a large conjugate functional group such as anthranilamino group or anthranyloxy group give rise to a resin which has a high refractive index but is extremely poor in transparency and vulnerable to discoloration upon heating and exposure to light.

Consequently, for the polymerizable monomer to give rise to a resin having both good transparency and high refractive indices, the groups $B^1$ and $B^2$ in it should preferably be the phenoxy group, naphthoxy group, or anilino group which may have respectively the group represented by Formula (3), Formula (4), and Formula (5).

In the meantime, Patent Documents 5 and 6 mentioned above describe polymers produced from a monomer capable of polymerization but free of aromatic rings, such as the one which is obtained by reacting cyanuric chloride with a (meth)acrylic ester having a hydroxyl group, thereby giving a monomer composed of triazine and three (meth)acrylic esters directly connected thereto. Because this monomer does not possess aromatic ring-containing substituents at all, the resulting resin does not have a high refractive index intended in the present invention.

The above-mentioned polymerizable monomer according to the present invention can be produced by any known organic synthetic reaction. The actual process consists of the reaction of cyanuric halide (such as cyanuric chloride) with amines or alcohols corresponding to A, $B^1$, and $B^2$ in the presence of an adequate organic solvent.

Raw materials for the reaction are commercially available.

The high-refractive-index resin composition according to the present invention may be a homopolymer of the polymerizable monomer represented by Formula (1) given above or a copolymer of said monomer with another polymerizable monomer.

The comonomer for this purpose is not specifically restricted so long as it has a functional group that reacts with the carbon-carbon double bond in the monomer of Formula (1), thereby giving rise to the desired copolymer. It includes, for example, vinyl monomer, acrylic monomer, methacrylic monomer, allyl monomer, and maleic acid monomer.

Examples of the vinyl monomer include aromatic vinyl compounds, such as styrene, divinylbenzene, vinylnaphthalene, and divinylnaphthalene; vinyl esters, such as vinyl acetate, vinyl versate, and vinyl adipate; vinyl ketones, such as vinyl methyl ketone and vinyl ethyl ketone; vinyl ethers, such as vinyl methyl ether and vinyl ethyl ether; and vinyl group containing silicones, such as polydimethylsiloxane having terminal vinyl groups, polydiphenylsiloxane having terminal vinyl groups, polydiphenylsiloxane having terminal vinyl groups, polydimethylsiloxane-polydiphenylsiloxane copolymer having terminal vinyl groups, polydimethylsiloxane having side-chain vinyl groups, polydimethylphenylsiloxane having side-chain vinyl groups, and polydimethylsiloxane-polydiphenylsiloxane copolymer having side-chain vinyl groups.

Examples of the acrylic monomer include acrylic acid and esters thereof, such as acrylic acid, methyl acrylate, octyl acrylate, and stearyl acrylate; epoxy acrylates, such as bisphenol epoxy acrylate (composed of bisphenol epoxy resin and acrylic acid bonded thereto), phenol novolac epoxy acrylate (composed of phenol novolac epoxy resin and acrylic acid bonded thereto), and cresol novolac epoxy acrylate (composed of cresol novolac epoxy resin and acrylic acid bonded thereto); polyester acrylates (composed of polyester (such as polyethylene phthalate and polybutylene phthalate) and acrylic acid bonded thereto); and urethane acrylates (composed of isophoronediisocyanate-based polyurethane or hexamethylenediisocyanate-based polyurethane and acrylic acid bonded thereto).

Examples of the methacrylic monomer include methacrylic acid and esters thereof, such as methacrylic acid, methyl methacrylate, octyl methacrylate, and stearyl methacrylate; epoxy methacrylates, such as bisphenol epoxy methacrylate (composed of bisphenol epoxy resin and methacrylic acid bonded thereto), phenol novolac epoxy methacrylate (composed of phenol novolac epoxy resin and methacrylic acid bonded thereto), and cresol novolac epoxy methacrylate (composed of cresol novolac epoxy resin and methacrylic acid bonded thereto); polyester methacrylates (composed of polyester (such as polyethylene phthalate and polybutylene phthalate) and methacrylic acid bonded thereto); and urethane methacrylates (composed of isophoronediisocyanate-based polyurethane or hexamethylenediisocyanate-based polyurethane and methacrylic acid bonded thereto).

Examples of the allyl monomer include aromatic ally esters, such as diallyl phthalate; and hetero-ring-containing allyl compounds, such as triallyl cyanurate and triallyl isocyanurate.

Examples of the maleic acid monomer include maleic acid and esters thereof, such as maleic acid, maleic anhydride, monomethyl maleate, and dimethyl maleate; unsaturated polyesters which are obtained by reaction of maleic anhydride with a polyol such as ethylene glycol and neopentylglycol; monomaleimides (such as phenyl maleimide and cyclohexyl maleimide) which are obtained by reaction of maleic anhydride with a monoamine; and bismaleimides such as diphenyl ether bismaleimide which is obtained by reaction of maleic anhydride with a diamine.

The polymerizable monomers exemplified above may be used alone or in combination with one another. It is also possible to use monomers of different type in combination.

In the case where the polymerizable monomer represented by Formula (1) is copolymerized with another polymerizable monomer, the ratio of copolymerization should preferably be such that the amount of the first monomer is 70 to 100 parts by weight (more preferably 80 to 100 parts by weight) and the amount of the second monomer is less than 30 parts by weight (more preferably less than 20 parts by weight), so that the resulting polymer has both good heat resistance and high refractive indices as intended in the present invention. The lower limit of the amount of the second monomer is not restricted so long as it is more than 0 parts by weight.

The high-refractive-index resin composition according to the present invention may be produced with the help of an activating agent such as radical polymerization initiator without specific restrictions.

Examples of the polymerization initiator include organic peroxides, such as benzoyl peroxide; azo-type initiator, such as azobisisobutyronitrile; and redox-type initiator, such as cumenehydroperoxide/cobalt naphthenate.

Any common radical initiators may be used without specific restrictions.

The amount of the polymerization initiator should be 0.1 to 10 parts by weight for 100 parts by weight of the polymerizable monomer.

The practical method for polymerization is not specifically restricted. Any known method may be selected from bulk polymerization, suspension polymerization, and solution polymerization, with the last one being preferable.

The organic solvent for solution polymerization is not specifically restricted so long as it permits polymerization or copolymerization of the polymerizable monomer of Formula (1). It includes, for example, amide-type solvents, such as dimethylacetamide and N-methylpyrrolidone; cyclic ether-type solvents, such as tetrahydrofuran; ketone-type solvents, such as methyl ethyl ketone and cyclohexanone; ester-type solvents, such as γ-butyrolactone; halogen-type solvents, such as dichloroethane; aromatic solvents, such as toluene and benzene; and mixed solvents thereof.

The solution polymerization yields a solution of resin composition, which can be used as such or after purification to remove a small amount of residual monomer. This purification may be accomplished by adding the solution of the resin composition into a poor solvent (such as alcohol and hydrocarbon) for reprecipitation of resin component, followed by filtration and drying, and then dissolving again the thus obtained resin component in organic solvents.

The resin composition obtained by bulk polymerization or suspension polymerization may be made into a resin solution by dissolution in an organic solvent.

The organic solvent for this purpose is not specifically restricted so long as it is capable of dissolving the resin composition. Its preferred examples include amide-type solvents, such as dimethylacetamide and N-methylpyrrolidone; cyclic ether-type solvents, such as tetrahydrofuran; ketone-type solvents, such as methyl ethyl ketone and cyclohexanone; and ester-type solvents, such as γ-butyrolactone.

As mentioned above, the high-refractive-index resin composition of the present invention is obtained in the form of solution. The solution is applied to a substrate, followed by drying, to give a transparent resin film having a refractive index higher than 1.57 at a wavelength of 633 nm.

The resin film obtained in this stage is thermoplastic. Therefore, the solution of the resin composition may be incorporated with a crosslinking agent so that the resin film improves in physical properties.

The crosslinking agent is not specifically restricted. It may be properly selected from those which are commonly used for resin compositions of this type. For example, it may be selected from epoxy compounds, isocyanate compounds, and aminoplast compounds. One or more species of them may be used.

Examples of the epoxy compound include liquid bisphenol-A type epoxy resin, solid bisphenol-A type epoxy resin, liquid bisphenol-F type epoxy resin, solid bisphenol-F type epoxy resin, phenol-novolac type epoxy resin, cresol-novolac type epoxy resin, hydrogenated bisphenol-A type epoxy resin, hydrogenated bisphenol-F type epoxy resin, triglycidyl isocyanurate, glycidyl methacrylate polymer, glycidyl methacrylate copolymer, and epoxidized soybean oil.

Examples of the isocyanate compound include polyfunctional isocyanate compounds, such as toluoylene diisocyanate, isophorone diisocyanate, hexamethylene diisocyanate, and diphenylmethane diisocyanate; and blocked isocyanates which are obtained by reaction of said isocyanate compound with caprolactam or oxime (which functions as a protective group).

Incidentally, the isocyanate compound should preferably be added to the solution of the resin composition immediately before use.

Examples of the aminoplast compound include urea resin, melamine resin, and benzoguanamine resin, each having two or more alkoxymethyl groups in the molecule. Preferable among these examples is melamine resin having two or more alkoxymethyl groups in the molecule.

The amount of the above-mentioned crosslinking agent to be used for 100 parts by weight of the solution of the resin composition should be 0.1 to 20 parts by weight, preferably 1 to 20 parts by weight, and more preferably 1 to 10 parts by weight.

The coating composition incorporated with the crosslinking agent in an amount specified above yields a resin film which has good transparency and high refractive indices, which are the major characteristic properties intended by the present invention, as well as good solvent resistance, good heat resistance, and good mechanical properties.

Incidentally, the above-mentioned crosslinking agent may optionally be used in combination with a crosslinking catalyst, which includes, for example, acid catalysts, such as acetic acid and paratoluenesulfonic acid, tertiary amine catalysts, such as triethylamine, quaternary amine catalysts, such as tetrabutylammonium bromide, and quaternary phosphonium catalysts, such as triphenylbenzylphosphonium chloride.

The amount of the crosslinking catalyst should be about 0.1 to 5 parts by weight for 100 parts by weight of the solids in the solution of the resin composition.

In the coating composition composed of the high-refractive-index resin composition (mentioned above) and an organic solvent and an optional crosslinking agent or crosslinking catalyst, solid content is preferably 0.5 to 50 wt %. The high-refractive-index resin contains preferably 60 to 100 wt %, more preferably 80 to 100 wt %, and further preferably 80 to 99.9 wt % in the solid.

The coating composition mentioned above may be applied to a substrate by means of a spin coater, spray coater, doctor blade, bar coater, or the like, followed by heating and curing at 100 to 250° C. with a heating device such as hot plate, hot air circulating drier, or infrared furnace, so that it is made into a resin film.

EXAMPLES

The invention will be described in more detail by way of the following Examples and Comparative Examples which are not intended to restrict the scope thereof. Incidentally, the following method was employed for determination of NMR spectra.

[$^1$H-NMR]

The sample of the compound is dissolved in a deuterated chloroform, and the resulting solution is examined for $^1$H-NMR at 400 MHz by using the apparatus made by Varian.

<Synthesis of Polymerizable Monomer>

Example 1

Synthesis of Polymerizable Monomer (M1)

(1) Synthesis of Intermediate Compound (L1)

[Chemical Formula 7]

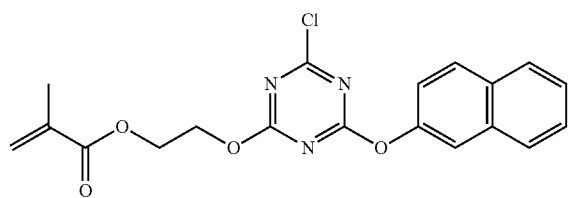

(L1)

In a 500-mL four-neck flask were placed cyanuric acid chloride (15.0 g), 2-hydroxyethyl methacrylate (12.7 g), and tetrahydrofuran (150 g). After cooling in an ice bath, sodium hydride (3.9 g) was added into the flask at 0° C. The reaction solution was stirred at room temperature for three hours. To the flask was further added an aqueous solution containing 2-naphthol (11.3 g) and sodium hydroxide (3.1 g) dissolved in water (120 g). The resulting solution was given an aqueous solution (15 wt %) of ammonium chloride, and the reaction product was extracted with ethyl acetate. After drying over anhydrous magnesium sulfate, the organic layer was filtered and solvent was removed from the filtrate with a rotary evaporator. The residues were purified by recrystallization. Thus there was obtained a white solid (14.1 g).

This white solid was examined for NMR, and the following result was obtained. The result suggests that the white solid is the intermediate compound represented by Formula L1.

$^1$H-NMR (400 MHz, CDCl$_3$): δ 7.92-7.80 (m, 3H), 7.62 (d, 1H), 7.55-7.48 (m, 2H), 7.29 (dd, 1H), 6.14-6.10 (m, 1H), 5.59-5.57 (m, 1H), 4.64-4.60 (m, 2H), 4.43-4.40 (m, 2H), 1.96-1.90 (m, 3H).

(2) Synthesis of Polymerizable Monomer (M1)

[Chemical Formula 8]

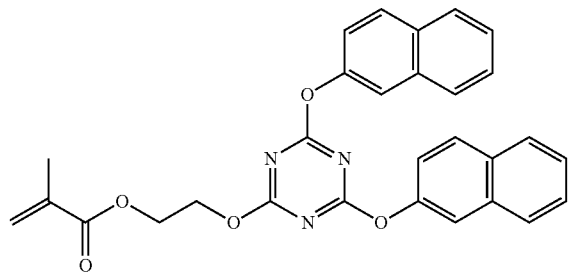

(M1)

In a 500-mL four-neck flask were placed the intermediate compound (L1) obtained as mentioned above (13.8 g) and acetone (260 mL). To the flask were added 2-naphthol (5.7 g), sodium hydroxide (1.6 g), and water (13 g) dropwise under refluxing. The resulting solution was given an aqueous solution (15 wt %) of ammonium chloride for precipitation. The resulting precipitates were filtered off and then recrystallized for purification. Thus there was obtained a white solid (12.3 g).

This white solid was examined for NMR, and the following result was obtained. The result suggests that the white solid is a polymerizable monomer represented by Formula M1.

$^1$H-NMR (400 MHz, CDCl$_3$): δ 7.90-7.78 (m, 4H), 7.78-7.71 (m, 2H), 7.61 (d, 2H), 7.55-7.44 (m, 4H), 7.30 (dd, 2H), 6.14-6.07 (m, 1H), 5.61-5.55 (m, 1H), 4.59-4.50 (m, 2H), 4.46-4.36 (m, 2H), 1.94-1.90 (m, 3H).

Example 2

Synthesis of Polymerizable Monomer (M2)

[Chemical Formula 9]

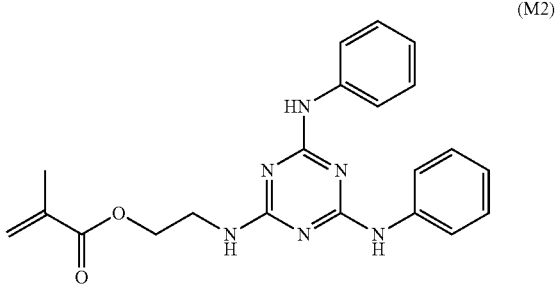

(M2)

In a 300-mL four-neck flask were placed cyanuric acid chloride (10.0 g) and acetone (80 mL). After cooling in an ice bath, aniline (10.6 g) and acetone (20 mL) were added to the flask at 0° C., then sodium carbonate (6.3 g) and water (20 mL) were added. The reaction solution was stirred at 0° C. for one hour and then stirred overnight at room temperature. The reaction solution underwent extraction with water and diethyl ether. After drying over anhydrous magnesium sulfate, the organic layer was filtered and solvent was removed from the filtrate with a rotary evaporator. The residues were washed with hexane and toluene. Thus there was obtained a white solid (14.5 g).

In a 300-mL three-neck flask were sequentially placed the white solid (14.5 g) obtained as mentioned above, tetrahydrofuran (220 mL), 2-aminoethanol (6.5 g), and triethylamine (10.8 g), followed by stirring overnight at 60° C. The reaction solution underwent extraction with water and diethyl ether. After drying over anhydrous magnesium sulfate, the organic layer was filtered and solvent was removed from the filtrate with a rotary evaporator. The residues were washed with a mixed solvent of hexane and diethyl ether. Thus there was obtained a white solid (14.8 g).

In a 200-mL three-neck flask were sequentially placed the white solid (7.7 g) obtained as mentioned above, dichloroethane (80 mL), N,N'-dicyclohexylcarbodiimide (5.9 g), 4-dimethylaminopyridine (4.4 g), and methacrylic acid (3.1 g), followed by stirring overnight at 90° C. The reaction solution underwent extraction with water and diethyl ether. After drying over anhydrous magnesium sulfate, the organic layer was filtered and solvent was removed from the filtrate with a rotary evaporator. The residues were purified by silica gel column chromatography and recrystallization. Thus there was obtained a white solid (4.2 g).

This white solid was examined for NMR, and the following result was obtained. The result suggests that the white solid is a polymerizable monomer represented by Formula M2.

$^1$H-NMR (400 MHz, CDCl$_3$): δ 7.56 (br, 4H), 7.36-7.27 (m, 4H), 7.13-7.00 (m, 4H), 6.13-6.10 (m, 1H), 5.59-5.56 (m, 1H), 5.40 (t, 1H), 4.33 (t, 2H), 3.78-3.73 (m, 2H), 1.94-1.93 (m, 3H).

Example 3

Synthesis of Polymerizable Monomer (M3)

[Chemical Formula 10]

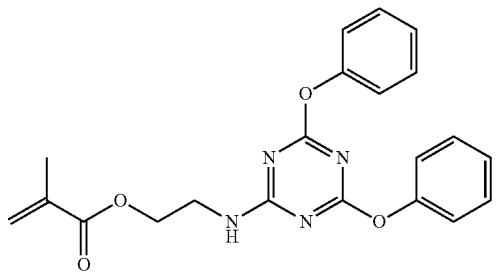

(M3)

In a 300-mL four-neck flask were placed cyanuric acid chloride (10.0 g) and tetrahydrofuran (80 mL). After cooling in an ice bath, phenol (10.7 g), sodium hydroxide (6.3 g), and water (50 mL) were added to the flask at 0° C. The reaction solution was stirred at 0° C. for one hour and then stirred overnight at room temperature. The reaction solution underwent extraction with water and diethyl ether. After drying over anhydrous magnesium sulfate, the organic layer was filtered and solvent was removed from the filtrate with a rotary evaporator. The residues were washed with hexane. Thus there was obtained a white solid (14.3 g).

In a 200-mL three-neck flask were placed sequentially the white solid (14.0 g) obtained as mentioned above, tetrahydrofuran (200 mL), 2-aminoethanol (4.3 g), and triethylamine (7.6 g), followed by stirring for 7 hours at 60° C. The reaction solution underwent extraction with water and diethyl ether. After drying over anhydrous magnesium sulfate, the organic layer was filtered and solvent were removed from the filtrate with a rotary evaporator. The residues were washed with a mixed solvent of hexane and ethyl acetate. Thus there was obtained a white solid (11.7 g).

In a 300-mL three-neck flask were sequentially placed the white solid (11.7 g) obtained as mentioned above, dichloroethane (120 mL), N,N'-dicyclohexylcarbodilmide (9.0 g), 4-dimethylaminopyridine (6.6 g), and methacrylic acid (3.7 g), followed by stirring overnight at room temperature. The reaction solution underwent extraction with water and diethyl ether. After drying over anhydrous magnesium sulfate, the organic layer was filtered and solvent was removed from the filtrate with a rotary evaporator. The residues were purified by using hexane and methanol. Thus there was obtained a white solid (10.5 g).

This white solid was examined for NMR, and the following result was obtained. The result suggests that the white solid is a polymerizable monomer represented by Formula M3.

$^1$H-NMR (400 MHz, CDCl$_3$): δ 7.39-7.33 (m, 4H), 7.24-7.18 (m, 2H), 7.18-7.10 (m, 4H), 6.10-6.06 (m, 1H), 5.89 (t, 1H), 5.59-5.56 (m, 1H), 4.22-4.19 (m, 2H), 3.65-3.60 (m, 2H), 1.95-1.89 (m, 3H).

Example 4

Synthesis of Polymerizable Monomer (M4)

(1) Synthesis of Intermediate Compound (L2)

[Chemical Formula 11]

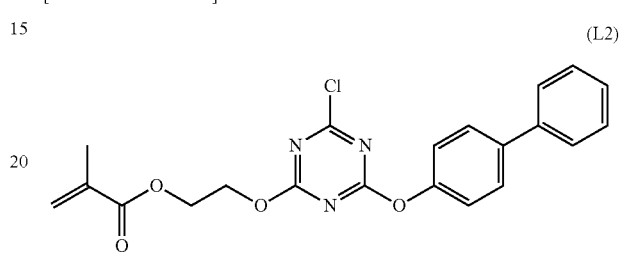

(L2)

In a 500-mL four-neck flask were placed cyanuric acid chloride (15.0 g), 2-hydroxyethyl methacrylate (12.7 g), and tetrahydrofuran (150 g). After cooling in an ice bath, sodium hydride (3.9 g) was added to the flask at 0° C. The reaction solution was stirred at room temperature for three hours. To the flask was further added an aqueous solution containing 4-phenylphenol (12.5 g), sodium hydroxide (2.9 g), and tetrahydrofuran (23 g) dissolved in water (30 g). The resulting solution was given an aqueous solution (15 wt %) of ammonium chloride, and the reaction product was extracted with ethyl acetate. After drying over anhydrous magnesium sulfate, the organic layer was filtered and solvent was removed from the filtrate with a rotary evaporator. The residues were purified by recrystallization. Thus there was obtained a white solid (21.7 g).

This white solid was examined for NMR, and the following result was obtained. The result suggests that the white solid is an intermediate compound represented by Formula L2.

$^1$H-NMR (400 MHz, CDCl$_3$): δ 7.67-7.55 (m, 4H), 7.47-7.33 (m, 3H), 7.27-7.21 (m, 2H), 6.14-6.09 (m, 1H), 5.62-5.57 (m, 1H), 4.68-4.62 (m, 2H), 4.48-4.44 (m, 2H), 1.96-1.90 (m, 3H).

(2) Synthesis of Polymerizable Monomer (M4)

[Chemical Formula 12]

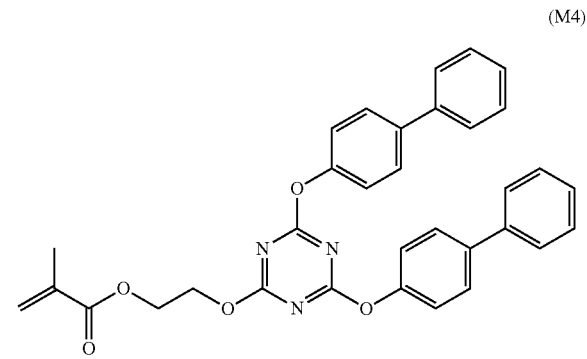

(M4)

In a 500-mL four-neck flask were placed the intermediate compound (L2) obtained as mentioned above (21.4 g) and acetone (170 g). 4-phenylphenol (9.3 g), sodium hydroxide (2.2 g), acetone (43 g), and water (43 g) were added dropwise to the flask under refluxing. The resulting solution was given an aqueous solution (15 wt %) of ammonium chloride for precipitation. The resulting precipitates were filtered off and then recrystallized for purification. Thus there was obtained a white solid (25.2 g).

This white solid was examined for NMR, and the following result was obtained. The result suggests that the white solid is a polymerizable monomer represented by Formula M4.

$^1$H-NMR (400 MHz, CDCl$_3$): δ 7.62-7.52 (m, 8H), 7.46-7.39 (m, 4H), 7.39-7.33 (m, 2H), 7.26-7.21 (m, 4H), 6.13-6.10 (m, 1H), 5.62-5.56 (m, 1H), 4.65-4.58 (m, 2H), 4.48-4.42 (m, 2H), 1.95-1.92 (m, 3H).

Example 5

Synthesis of Polymerizable Monomer (M5)

[Chemical Formula 13]

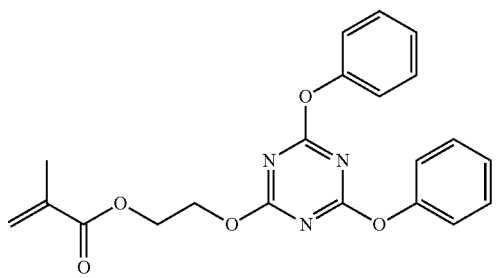

(M5)

In a 500-mL four-neck flask were placed cyanuric acid chloride (15.0 g), 2-hydroxyethyl methacrylate (12.7 g), and tetrahydrofuran (150 g). After cooling in an ice bath, sodium hydride (3.9 g) was added to the flask at 0° C. The reaction solution was stirred for three hours at room temperature. To the flask was further added an aqueous solution of phenol (14.9 g) and sodium hydroxide (6.3 g) dissolved in water (60 g). The reaction solution was stirred for two hours at 50° C. After cooling to room temperature, the reaction solution was given an aqueous solution (15 wt %) of ammonium chloride, and underwent extraction with ethyl acetate. After drying over anhydrous magnesium sulfate, the organic layer was filtered and solvent was removed from the filtrate with a rotary evaporator. The residues were purified by silica column chromatography. Thus there was obtained a white solid (20.5 g).

This white solid was examined for NMR, and the following result was obtained. The result suggests that the white solid is a polymerizable monomer represented by Formula M5.

$^1$H-NMR (400 MHz, CDCl$_3$): δ 7.43-7.34 (m, 4H), 7.28-7.22 (m, 2H), 7.19-7.12 (m, 4H), 6.14-6.08 (m, 1H), 5.60-5.55 (m, 1H), 4.58-4.52 (m, 2H), 4.42-4.37 (m, 2H), 1.94-1.90 (m, 3H).

Example 6

Synthesis of Polymerizable Monomer (M6)

[Chemical Formula 14]

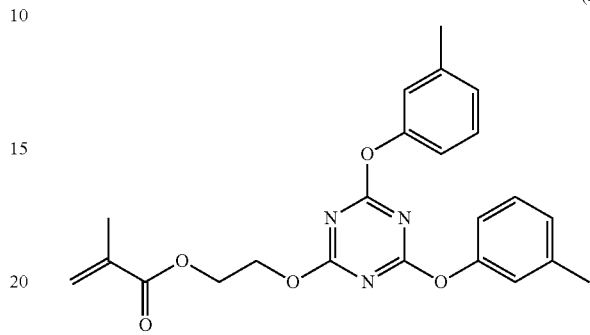

(M6)

In a 500-mL four-neck flask were placed cyanuric acid chloride (15.0 g), 2-hydroxyethyl methacrylate (12.7 g), and tetrahydrofuran (150 g). After cooling in an ice bath, sodium hydride (3.9 g) was added to the flask at 0° C. The reaction solution was stirred for three hours at room temperature. To the flask was further added an aqueous solution of 3-cresol (17.1 g), sodium hydroxide (6.3 g), and tetrahydrofuran (57 g) dissolved in water (75 g). The reaction solution was stirred for two hours at 50° C. After cooling to room temperature, the reaction solution was given an aqueous solution (15 wt %) of ammonium chloride, and underwent extraction with ethyl acetate. After drying over anhydrous magnesium sulfate, the organic layer was filtered and solvent was removed from the filtrate with a rotary evaporator. The residues were purified by silica column chromatography. Thus there was obtained a white solid (22.5 g).

This white solid was examined for NMR, and the following result was obtained. The result suggests that the white solid is a polymerizable monomer represented by Formula M6.

$^1$H-NMR (400 MHz, CDCl$_3$): δ 7.29-7.23 (m, 2H), 7.08-7.03 (m, 2H), 6.98-6.92 (m, 4H), 6.14-6.08 (m, 1H), 5.62-5.57 (m, 1H), 4.59-4.53 (m, 2H), 4.43-4.38 (m, 2H), 2.35 (s, 6H), 1.95-1.90 (m, 3H).

<Production of Resin Solution (Composition)>

Example 7

In a three-neck flask provided with a nitrogen inlet (capillary tube) were placed the polymerizable monomer M1 (21.0 g) obtained in Example 1, butyl acrylate (7.5 g), acrylic acid (1.5 g), and cyclohexanone (69 g) as a solvent. Nitrogen (2 L) was introduced into the reaction solution by bubbling through the capillary tube. With the capillary tube removed, air in the flask was purged by a small amount of nitrogen introduced into the gas phase in the flask. With the flask heated to 85° C. (inside temperature), the reaction solution was given 1,1-di (t-hexylperoxy)-3,3,5-cyclohexane (0.3 g) as a polymerization initiator. The polymerization reaction was continued for three hours at 85° C. After that, the reaction system was kept at 115° C. for two hours for aging, followed by cooling to room temperature. Thus there was obtained the high-refractive-index resin (P1) in the form of solution.

Examples 8 to 12

The same procedure as in Example 7 was repeated for solution polymerization to produce the solution of high-refractive-index resin, with the type and amount of solvent and polymerization initiator unchanged except that the polymerizable monomers obtained in Examples 2 to 6 were varied in amount as shown in Table 1.

In Example 9, however, the procedure was modified such that the reaction product was slowly added to methanol (2 L) with stirring for reprecipitation of the resin component, and the precipitates were filtered off by suction, followed by vacuum drying overnight. The resulting white powder (15 g) was dissolved in cyclohexanone (35 g) to give the solution of the high-refractive-index resin (P3).

Comparative Example 1

The same procedure as in Example 7 was repeated for solution polymerization to produce the solution of the comparative high-refractive-index resin (Q1), with the type and amount of solvent and polymerization initiator unchanged except that the polymerizable monomer obtained in Example 4 was used in an amount as shown in Table 1.

TABLE 1

| | Designation of resin | Polymerizable monomer of Formula (1) | | Additional polymerizable monomer | |
|---|---|---|---|---|---|
| | | Designation | Amount (g) | Designation | Amount (g) |
| Example 7 | P1 | M1 | 21.0 | BUA | 7.5 |
| | | | | AA | 1.5 |
| Example 8 | P2 | M2 | 30.0 | — | — |
| Example 9 | P3 | M3 | 28.5 | AA | 1.5 |
| Example 10 | P4 | M4 | 28.5 | MAA | 1.5 |
| Example 11 | P5 | M5 | 28.5 | MAA | 1.5 |
| Example 12 | P6 | M6 | 28.5 | HEMA | 1.5 |
| Comparative Example 1 | Q1 | M4 | 15.0 | MMA | 13.5 |
| | | | | MAA | 1.5 |

BUA: Butyl acrylate
AA: Acrylic acid
MAA: Methacrylic acid
MMA: Methyl methacrylate
HEMA: 2-hyroxyethyl methacrylate <Production of Coating Material of High-Refractive-Index Resin>

Examples 13 to 18 and Comparative Example 2

Each of the resin solutions prepared in Examples 7 to 12 and Comparative Example 1 was incorporated with a crosslinking agent and optional components (such as catalyst) according to the composition shown in Table 2, so as to give the coating materials of high-refractive-index resin (designated as C1 to C6 and D1, respectively).

The crosslinking agent was added in the form of solution in cyclohexanone. In addition, the coating materials were prepared such that the total solid content was 30 wt %.

The coating material was used after dilution with a solvent (cyclohexanone) according to coating conditions.

TABLE 2

| | Designation of coating material | Resin solution | | Crosslinking agent | | Other components | |
|---|---|---|---|---|---|---|---|
| | | Designation | Solids (pbw) | Designation | Solids (pbw) | Designation | Amount (pbw) |
| Example 13 | C1 | P1 | 100 | YX-8000 | 5 | — | — |
| Example 14 | C2 | P2 | 100 | CYMEL303 | 10 | Acetic acid | 1.0 |
| Example 15 | C3 | P3 | 100 | YX-8000 | 5 | — | — |
| Example 16 | C4 | P4 | 100 | YX-8000 | 5 | — | — |
| Example 17 | C5 | P5 | 100 | YX-8000 | 5 | — | — |
| Example 18 | C6 | P6 | 100 | VESTANAT-B 1358/100 | 10 | — | — |
| Comparative Example 2 | D1 | Q1 | 100 | YX-8000 | 5 | — | — |

YX-8000: Hydrogenated bisphenol-A epoxy resin (from Japan Epoxy Resin Corp.)
CYMEL 303: Alkoxymethylated melamine resin (from Mitsui Saitec Corp.)
VESTANAT-B 1358/100: Modified isophorone diisocyanate-based block isocyanate (from Degussa Corp.)

Each of the coating materials (C1 to C6) of high-refractive-index resins prepared in Examples 13 to 18 and the comparative coating material (D1) prepared in Comparative Example 2 was made into a coating film, and the resulting coating film was examined for light transmission, refractive index, solvent resistance, and resistance to liquid resin, in the following manner. The results are shown in Table 3.

(1) Light Transmission

Each sample of the coating materials was applied to a quartz plate (4×4 cm) by using a spin coater. After drying for one hour at 100° C. and curing for one hour at 150° C., there was obtained a coating film having a thickness of 5 μm.

The thus obtained coating film was examined for light transmission at a wavelength of 400 nm by using a spectrophotometer UV-3100PC made by Shimadzu Corp.

(2) Refractive Index

Each sample of the coating materials was applied to a silicon wafer by using a spin coater. After drying for one hour at 100° C. and curing for one hour at 150° C., there was obtained a coating film having a thickness of 100 nm.

The thus obtained coating film was examined for refractive index at a wavelength of 633 nm by using an automatic ellipsometer DVA-FLVW made by Mizojiri Kogaku Kogyosho Co., Ltd.

(3) Solvent Resistance

Each sample of the coating materials was applied to a silicon wafer by using a spin coater. After drying for one hour at 100° C. and curing for one hour at 150° C., there was obtained a coating film having a thickness of 1 μm.

The silicon wafer with a coating film (1 μm thick) was immersed in N-methylpyrrolidone (NMP) for 3 minutes and then heated for 1 minute at 200° C. for solvent removal (or drying).

The dried coating film was examined for thickness and rated for solvent resistance in terms of the film retaining ratio (which is defined as film thickness after test divided by film thickness before test multiplied by 100). The sample with a film retaining ratio higher than 60% or lower than 60% is rated as "good" or "poor," respectively.

(4) Resistance to Liquid Resin

A sample of clear epoxy resin composition was prepared in the following manner from 10 g of hydrogenated bisphenol-A epoxy resin ("YX-8000"), from Japan Epoxy resin Corp., 8.0 g of methylated hexahydrophthalic anhydride as a curing agent, and 0.2 g of quaternary phosphonium salt ("U-CAT SA-5003") as a catalyst, from San-Apro Ltd. These ingredients were placed in a sealable glass vial. The vial was tightly sealed, with its space filled with nitrogen, and the contents were stirred for one hour by a magnetic stirrer. Thus there was obtained a clear epoxy resin composition.

This clear epoxy resin composition (0.1 g) was placed on the coating film formed on the quartz plate (for measurement of light transmission) by using a pipet so that a hemispherical droplet was formed. This procedure was repeated five times, so that five hemispheric droplets were randomly formed on the coating film.

Then, the test piece was placed in a drying machine so that the droplets were cured at 90° C. for one hour, 105° C. for two hours, and 150° C. for three hours. After heating, the test piece was allowed to cool slowly overnight. The interface between the coating film and the semispherical cured product of epoxy resin was examined.

The sample is rated as "good" if all of the five droplets showed no sign of peeling from the coating film and exhibited good adhesion to the coating film, and their interface retained good transparency without opacity and deformation and there is no peeling in the interface between the quartz plate and the coating film (C1). Otherwise, the sample is rated as "poor."

TABLE 3

| Coating material | Light transmission (%) | Refractive index | Solvent resistance | Resistance to liquid resin |
|---|---|---|---|---|
| Example 13 | C1 | 96.8 | 1.6029 | Good (94%) | Good |
| Example 14 | C2 | 96.0 | 1.6464 | Good (89%) | Good |
| Example 15 | C3 | 97.8 | 1.5864 | Good (100%) | Good |
| Example 16 | C4 | 96.9 | 1.6185 | Good (80%) | Good |
| Example 17 | C5 | 97.7 | 1.5775 | Good (88%) | Good |
| Example 18 | C6 | 96.8 | 1.5730 | Good (66%) | Good |
| Comparative Example 2 | D1 | 99.9 | 1.5595 | Good (67%) | Good |

Comparative Example 3

Synthesis of Polymerizable Monomer (M7)

In a 500-mL four-neck flask were placed cyanuric acid chloride (12.0 g), 2-hydroxyethyl methacrylate (9.3 g), and tetrahydrofuran (96 g). After cooling in an ice bath, sodium hydride (3.4 g) was added to the flask at 0° C. The reaction solution was stirred for one hour at room temperature. To the flask was further added a solution of diethylamine (20.9 g) dissolved in tetrahydrofuran (24 g), followed by stirring for two hours at 50° C. After cooling to room temperature, the reaction solution underwent extraction with 1N hydrochloric acid and ethyl acetate. After drying over anhydrous magnesium sulfate, the organic layer was filtered and solvent was removed from the filtrate with a rotary evaporator. The residues were purified by silica column chromatography. Thus there was obtained a white solid (23 g).

This white solid was examined for NMR, and the following result was obtained. The result suggests that the white solid is a polymerizable monomer represented by Formula M7. The polymerizable monomer M7 was used for production of the comparative coating material mentioned later.

$^1$H-NMR (400 MHz, CDCl$_3$): δ 6.16-6.12 (m, 1H), 5.58-5.55 (m, 1H), 4.57-4.53 (m, 2H), 4.51-4.45 (m, 2H), 3.55 (q, 8H), 1.95-1.92 (m, 3H), 1.16 (t, 12H).

[Chemical Formula 15]

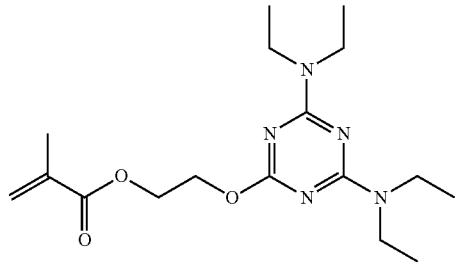

(M7)

Comparative Example 4

The same procedure as in Example 8 was repeated for solution polymerization except that the polymerizable monomer M2 was replaced by the polymerizable monomer M7 obtained in Comparative Example 3. The resulting product was designated as Comparative resin solution Q2.

TABLE 4

| | Designation of resin | Polymerizable monomer containing triazine ring | | Other polymerizable monomer | |
|---|---|---|---|---|---|
| | | Designation | Amount (g) | Designation | Amount (g) |
| Comparative Example 4 | Q2 | M7 | 30.0 | — | — |

<Production of Coating Material of High-Refractive-Index Resin>

The same procedure as in Example 14 was repeated to produce the coating material D2 except that the resin Q2 was used.

Comparative Example 5

Synthesis of Polymerizable Monomer Composition

Patent Document 5 mentioned above discloses Example 2 which is intended to give a polymerizable monomer composition in which the polymerizable monomer represented by Formula M8 below accounts for 88 wt %.

A polymerizable monomer (for comparison) was synthesized as follows in the same way as disclosed in Example 2 of Patent Document 5, with the compositional ratio, temperature conditions, and post treatment (such as washing) kept unchanged.

In a 300-mL four-neck flask were placed toluene (67.6 g), cyanuric acid chloride (20.0 g), 2-hydroxyethyl methacrylate (48.4 g), sodium carbonate (87.6 g), and N-nitrosodiphenylamine (0.0048 g) as a polymerization inhibitor. The contents in the flask were stirred at 25° C. for four hours and then for two hours at 90° C. After cooling to 60° C., the flask was given triethylamine (5.6 g), followed by stirring for two hours. The resulting reaction mixture in slurry form was given water (500 g), followed by stirring for dissolution of inorganic matter. The resulting solution was allowed to stand for liquid separation. The organic layer was poured into water (120 g), and the aqueous layer was neutralized (to pH 4) with 5N hydrochloric acid. The organic layer was separated and washed twice with water (120 g each). The organic layer was separated and dehydrated and dried over anhydrous magnesium sulfate (2 g) and finally freed of toluene by vacuum distillation. Thus there was obtained a light yellowish clear viscous liquid (24 g), which is the polymerizable monomer composition described in Example 2 of Patent Document 5.

[Chemical Formula 16]

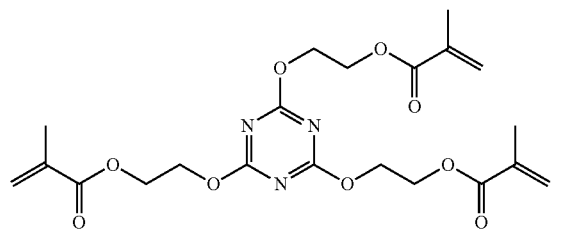

(M8)

<Production of Coating Material of High-Refractive-Index Resin>

Comparative Example 6

As mentioned above, Comparative Example 5 gave the same polymerizable monomer composition as disclosed in Example 2 of Patent Document 5. Unfortunately, the resulting product is polyfunctional and hence subject to crosslinking and gelation in solution polymerization. Therefore, the polymerizable monomer composition (Q3) obtained in Comparative Example 5 was made into a photocurable resin composition without undergoing solution polymerization.

That is, 100 g of Q3 was mixed with a solution of 2 g of DAROCURE-1173 (a product of Ciba Corp.) dissolved in 400 g of propylene glycol monomethyl ether (PGME for short hereinafter). The resulting mixture is the photocurable resin coating material (D3) shown in Table 5.

TABLE 5

| | Name of coating material | Resin solution | | Crosslinking agent | | Other components | |
|---|---|---|---|---|---|---|---|
| | | Name | Solids (pbw) | Name | Solids (pbw) | Name | Amount (pbw) |
| Comparative Example 4 | D2 | Q2 | 100 | CYMEL 303 | 10 | Acetic acid | 1 |
| Comparative Example 6 | D3 | Q3 | 100 | DAROCURE-1173 | 2 | PGME | 400 |

CYMEL 303: Alkoxymethylated melamine resin (a product of Mitsui Saiteck Corp.)
DAROCURE-1173: Photopolymerization initiator (a product of Ciba Corp.)

The coating solution (D2) prepared in Comparative Example 4 was made into coating film by curing in the same way as in Example 13. The coating film was examined for light transmission, refractive index, solvent resistance, and resistance to liquid resin in the same way as mentioned above.

The coating solution (D3) prepared in Comparative Example 6 was applied to a quartz plate (4×4 cm) or a silicon wafer by using a spin coater. This coating step was followed by irradiation with light from a metal halide lamp at a wavelength of 350 nm and with a dose of 999 mJ in a nitrogen atmosphere. This irradiation step was followed by drying for 5 minutes at 150° C. The coating film was examined for light transmission, refractive index, solvent resistance, and resistance to liquid resin in the same way as mentioned above. The results are shown in Table 6.

TABLE 6

| | Coating material | Light transmission (%) | Refractive index | Solvent resistance | Resistance to liquid resin |
|---|---|---|---|---|---|
| Comparative Example 4 | D2 | 99.1 | 1.5355 | Poor (0%) | Poor |
| Comparative Example 6 | D3 | 97.4 | 1.5386 | Good (99%) | Good |

As shown in Table 3, each of the transparent high-refractive-index coating materials (C1 to C6) prepared in Examples 13 to 18 gave a coating film having high clarity as well as high refractive indices exceeding 1.57 at a wavelength of 633 nm, despite the fact that it is composed only of four elements (carbon, hydrogen, oxygen, and nitrogen).

Not only does the coating film excel in solvent resistance but it also excels in stability during curing with liquid resins and adhesion to the cured product of the liquid resin and to the inorganic materials such as quartz.

By contrast, as shown in Tables 3 and 6, each of the coating materials D1 to D3 obtained in Comparative Examples 2, 4, and 6 gave coating films which are good in transparency but low in refractive index.

As explained above, the coating material containing the resin composition according to the present invention exhibits good adhesion to inorganic materials as well as organic materials. It also excels in solvent resistance and it remains intact (without dissolution and peeling) when a liquid resin cures in contact with it. This property is useful in application to the field of optoelectronic materials, such as coating on light-emitting diodes, CCD or CMOS sensors, photocouplers, solar cells, lenticular lenses, and waveguides.

The coating material will find use not only in the optoelectronic field but also in the field of industrial materials such as glass and plastic lenses.

The invention claimed is:
1. A polymerizable monomer having a 1,3,5-triazine ring represented by Formula (1) below:

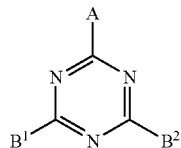
(1)

where A denotes a group represented by Formula (2) below,

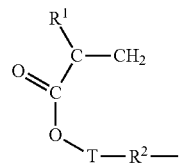
(2)

in which $R^1$ denotes a hydrogen atom or methyl group, T denotes a $C_{1-10}$ alkylene group, and $R^2$ denotes O or NH; and $B^1$ and $B^2$ mutually independently denote those groups represented by Formula (3), Formula (4), or Formula (5) below,

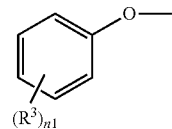
(3)

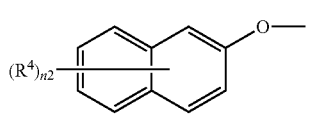
(4)

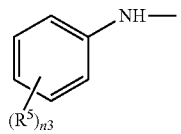
(5)

in which $R^3$ denote a $C_{1-10}$ alkyl group or aryloxy group, $R^4$ and $R^5$ each denote a $C_{1-10}$ alkyl group, aryl group, or aryloxy group, n1 and n3 are integers of 0 to 5, and n2 is an integer of 0 to 7, provided that $R^3$, $R^4$, and $R^5$ each in plural numbers may be identical with or different from one another.

2. A high-refractive-index resin composition which is obtained by copolymerization of 70 to 100 parts by weight of the polymerizable monomer having a 1,3,5-triazine ring represented by Formula (1) below, 0 to 30 parts by weight of additional polymerizable monomer,
wherein said composition contains 0.1 to 20 parts by weight of at least one species of crosslinking agent selected from epoxy compounds, isocyanate compounds, and aminoplast compounds, for 100 parts by weight of the resin in the resin composition:

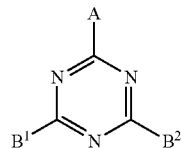
(1)

where A denotes a group represented by Formula (2) below,

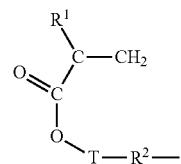
(2)

in which $R^1$ denotes a hydrogen atom or methyl group, T denotes a $C_{1-10}$ alkylene group, and $R^2$ denotes O or NH; and $B^1$ and $B^2$ mutually independently denote those groups represented by Formula (3), Formula (4), or Formula (5) below,

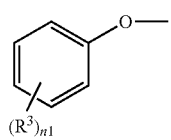
(3)

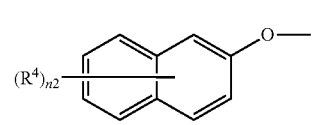
(4)

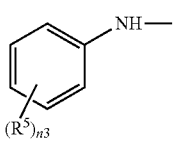
(5)

in which $R^3$ denote a $C_{1-10}$ alkyl group or aryloxy group, $R^4$, and $R^5$ each denote a $C_{1-10}$ alkyl group, aryl group, or aryloxy group, or aryloxy group, n1 and n3 are integers of 0 to 5, and n2 is an integer of 0 to 7, provided that $R^3$, $R^4$, and $R^5$ each in plural numbers may be identical with or different from one another.

3. The high-refractive-index resin composition according to claim 2 above in which the additional polymerizable monomer is at least one species selected from vinyl monomer, acrylic monomer, methacrylic monomer, allyl monomer, and maleic acid monomer.

* * * * *